United States Patent [19]

Blem et al.

[11] Patent Number: 4,528,022

[45] Date of Patent: Jul. 9, 1985

[54] DEFOLIATING COMPOSITION

[75] Inventors: Allen R. Blem, Cheshire; James A. McGuinness, Naugatuck, both of Conn.

[73] Assignee: Uniroyal, Inc., Middlebury, CT

[21] Appl. No.: 552,239

[22] Filed: Nov. 15, 1983

[51] Int. Cl.[3] .................... A01N 47/36; C07D 285/12
[52] U.S. Cl. .......................................... 71/73; 548/140
[58] Field of Search ............................ 548/140; 71/73

[56] References Cited

U.S. PATENT DOCUMENTS 4,175,081 11/1979 Driscoll .............................. 548/140
4,217,459 8/1980 Kirkpatrick ........................ 548/140

FOREIGN PATENT DOCUMENTS 3116008 10/1982 Fed. Rep. of Germany .......... 71/73
3116071 11/1982 Fed. Rep. of Germany .......... 71/73

Primary Examiner—Robert Gerstl
Attorney, Agent, or Firm—John A. Shedden

[57] ABSTRACT

A defoliating composition comprising a compound have the structural formula

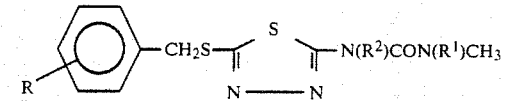

wherein R is F, Cl, 3-Br, 4-Br, I, CN or $CX_3$, where X is F, Cl or Br; $R^1$ is hydrogen or $C_1$–$C_4$ alkyl; and $R^2$ is $C_1$–$C_4$ alkyl and a carrier for said compound is disclosed.

6 Claims, No Drawings

DEFOLIATING COMPOSITION

BACKGROUND OF THE DISCLOSURE

1. Field of the Invention

The present invention is directed to new and known substituted thiadiazole ureas. More specifically, the instant invention is directed to substituted thiadiazole ureas compositions useful as defoliants.

2. Description of the Prior Art

Certain substituted thiadiazole ureas are known in the art. For example, thiadiazole ureas having benzylthio substituents, substituents carrying halo, trifluoromethyl and other groups have been disclosed to be herbicidally active in U.S. Pat. Nos. 4,066,436; 4,141,717; and 4,217,459, all issued to Kirkpatrick. None of these patents disclose, suggest or make obvious the use of these compounds for defoliating plants.

U.S. Pat. No. 4,175,081, issued to Driscoll, discloses the use of other substituted thiadiazole ureas, such substitutions being among others p-chlorobenzylthio groups. Driscoll discloses the herbicidal use of these compounds. This reference, however, does not disclose, suggest or mention any defoliating efficacy, and certainly not any cotton defoliating efficacy, for any of the compounds disclosed in his patent.

As those skilled in the art are aware, herbicidal use of a compound involves the phytotoxic effect of that compound on plants. A compound possessing phytotoxic properties causes plant tissue death, including the destruction of stems and leaves. However, the leaves of the plant subject to such phytotoxicity usually remain attached to the main body of the plants. Eventually, the plant collapses and falls to the ground.

On the other hand, as those skilled in the art are also aware, a defoliant is selective in its destructive effect on a plant. A defoliant affects only the leaves of the plant, causing them to mature, while the main body of the plant, i.e., the stems, roots, and fruiting bodies remain essentially undisturbed. In many instances, regrowth of new leaves begins some time after application of the defoliant.

It is most important, however, that the use of a chemical defoliant be specific. That is, the effect of the defoliant should be limited to the elimination of leaves from the plant. In many instances, defoliants act in a manner similar to that of a herbicide. In those cases not only are the leaves eliminated from the plant, but, undesirably, the plant itself collapses prior to harvesting.

The importance of defoliation in the harvesting of certain crops cannot be overemphasized. Probably the best example of a crop where defoliation is critical to the success of a harvest is cotton. Even under the most optimum conditions cotton plants do not mature uniformly or soon enough to facilitate mechanical harvesting. That is, cotton bolls do not appear before the growth of leaves on the cotton plants. Unlike other crops which may be easily mechanically harvested, the leaves of the cotton plants interfere with mechanical harvesting of lint from cotton bolls. When the cotton plant is leafy, mechanical pickers cannot be efficiently utilized. This is because the leaves interfere with the actual picking process. Furthermore, the leaves cause excess trash accumulations. In addition, the green leaves stain the cotton fiber.

Cotton defoliation eliminates the leaves which thus eliminate the interference in the picking process, elimination of excess trash as well as the prevention of fiber staining. Moreover, a defoliated plant permits the cotton bolls to mature, allowing a "once through the field" type of harvest. Those skilled in the art are aware this type of cotton harvesting is most efficient.

SUMMARY OF THE INVENTION

It has now been found that certain substituted thiadiazole ureas act as excellent defoliants. While acting as defoliants these substituted thiadiazole ureas do not exhibit extreme phytotoxic effects on the plants to which they are applied. These properties are particularly exhibited on cotton plants. The use of the substituted thiadiazole ureas of this invention permit mechanical harvesting of cotton plants. Leaf interference is eliminated, thus eliminating also excess trash accumulation and cotton fiber staining. The application of this defoliant to cotton, morever, enhances top cotton boll maturity which allows "once through the field" harvesting.

In accordance with the instant invention a defoliant composition comprising a compound having the structural formula

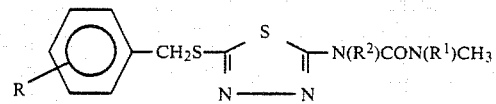

wherein R is F, Cl, 3-Br, 4-Br, I, CN or $CX_3$, where X is F, Cl or Br; $R^1$ is hydrogen or $C_1$–$C_4$ alkyl, and $R^2$ is $C_1$–$C_4$ alkyl is disclosed.

DETAILED DESCRIPTION

The defoliating composition of the instant invention is a compound having the structural formula

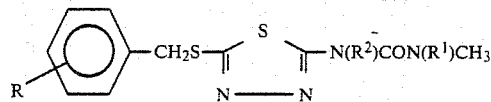

wherein R is fluorine, chlorine, 3-bromo, 4-bromo, iodine, cyano or $CX_3$ where X is fluorine, chlorine or bromine; R is hydrogen or $C_1$–$C_4$ alkyl; and $R^2$ is $C_1$–$C_4$ alkyl; and a carrier therefor.

More preferably, the compound of this composition is defined by R being fluorine, chlorine, 3-bromo, 4-bromo, $CF_3$ or $CCl_3$; $R^1$ is hydrogen or methyl; and $R^2$ is methyl.

Most preferably, the compound of this composition is characterized by the following definitions: R is 3-fluorine, 3-bromine, 3-chlorine or 3-$CF_3$; $R^1$ is hydrogen; and $R^2$ is methyl.

The carrier of the composition of this invention is a finely divided or granular organic or inorganic inert material well known to the art. Among the carriers preferred in this invention are attapulgite clay, sand, vermiculite, corn cobs and activated carbon.

In a preferred embodiment, the composition is formed as a wettable powder. In this embodiment the active agent, the substituted thiadiazole urea, is ground to a fine powder and mixed with an inert powdered carrier. Preferred powdered carriers that may be used in this embodiment include the mineral silicates, e.g., mica, talc, pyrophyllite and clay. A surface active dispersing agent is usually added to the active and inert powders. This wettable powder is dispersed in water and sprayed onto the plants to be defoliated.

In another preferred embodiment the carrier is an organic solvent, preferably an aliphatic or aromatic hydrocarbon such as benzene or toluene. In this embodiment an emulsifiable concentrate is formed by dissolving the substituted thiadiazole urea in the solvent to which a surface active dispersing agent has been added. The emulsifiable concentrate solution is added to water and the resultant emulsion is sprayed onto the plants.

In yet another preferred embodiment the inert carrier is water. In this embodiment the substituted thiadiazole urea is dissolved in water. The substituted thiadiazole ureas of this composition are slightly soluble in water, up to about 3,000 ppm (parts per million). This concentration may be increased by the addition of a cosolvent. The cosolvent may be acetone, dimethyl sulfoxide or other water miscible solvent. This water solution is sprayed onto the plants subsequent to the addition of a suitable surface active agent.

The surface active agent introduced into these spraying compositions improve the wettability of the composition. Improved wettability increases the absorption of the defoliant into the plant system. Suitable surface active agents, also referred to as surfactants, useful in this application are well known to those skilled in the art. Standard texts provide details of those surfactants within the contemplation of this invention. Among these references are McCutcheon's detergents and emulsifiers, 1970, Allured Publishing Corp., Ridgewood, N.J. In addition, U.S. Pat. No. 2,614,916 discloses such surfactants at columns 2–4. Also, U.S. Pat. No. 2,547,724 at columns 3 and 4 provides further details of these surfactants. These references are incorporated herein by reference.

The concentration of active agent, the compound of the composition, in the composition of this invention may vary widely, e.g. from 1 to 95% by weight. The concentration of the compound in sprays applied to the foliage also varies depending upon application. This range is from 0.002% to 75% by weight based on the total weight of the spray.

For defoliating plants 0.05 to 2.5 kilograms per hectare (kg/ha) of the compound of this invention may be used. Preferably, 0.1 to 1.0 kg/ha suffices and more preferably 0.25 to 0.85 kg/ha is used. The most suitable rate of application depends on such factors as physiological state of the plant, crop species and cultivar, soil type, soil pH, soil organic matter content, quantity and intensity of rainfall before and after treatment, air and soil temperatures, light intensity and light duration per day.

The plants which are particularly suited to the defoliant treatment provided by the composition of this invention include cotton, potato, sunflower, sugarbeets, peppers, tomato, grape, soybean, dry bean, oilseed ropo or canola, etc. All of these plants are defoliated without destroying these plants and at economically feasible application rates.

This invention is also directed to a new class of compounds having the structural formula

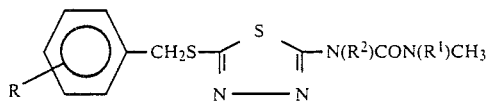

wherein R is 2-fluoro, 2-chloro, 2-iodo, 2-cyano or 2-$CX_3$ where X is F, Cl, or Br; $R^1$ is hydrogen or $C_1$–$C_4$ alkyl and $R^2$ is $C_1$–$C_4$ alkyl.

More preferably, the compound of this invention is defined by R being 2-fluoro or 2-chloro. Still more preferably, the compound is characterized by $R^1$ being hydrogen or methyl and $R^2$ being methyl.

The new compounds of this invention are prepared by reacting a 2-halo benzyl halide, preferably a substituted benzyl bromide, with 2-methylamino-1,3,4-thiadiazole-5-thiol in the presence of a suitable base, such as sodium ethoxide, in an appropriate solvent. A preferred solvent in this reaction is ethanol. The product of this reaction is the intermediate, 2-methylamino-5-2-halo benzylthio-1,3,4-thiadiazole. The intermediate is treated with methyl isocyanate in a suitable solvent, i.e., ethyl acetate, to form the desired (substituted) benzylthiothiadiazoleurea compound. Alternatively, the intermediate may be converted to the corresponding carbamoyl chloride by well known methods, subsequently introducing methyl or dimethylamine resulting in 1,3-dimethyl- or 1,1,3-trimethyl-3-(5-(substituted benzylthio)-1,3,4-thiadiazol-2-yl)ureas.

Still another method comprises reacting said intermediate with a dimethylcarbamoyl halide (e.g. chloride) in an inert solvent, preferably in the presence of an acid acceptor (e.g. pyridine), resulting in the 1,1,3-trimethyl-3-(5-(substituted benzylthio)-1,3,4-thiadiazol-2-yl)urea, also called N-(5-((substituted phenyl)methylthio)-1,3,4-thiadiazole-2-yl)-N,N'-dimethylurea.

The following examples are provided to illustrate the instant invention. The invention should not, therefore, be deemed to be limited thereto.

EXAMPLE 1

(A)

Preparation of 5-[(3-fluorophenyl)methylthio]-2-methylamine-1,3,4-thiadiazole

To a stirred solution of 8.5 g (0.157 mol) of sodium methoxide in an ethanol-methanol mixture (prepared by adding 36 ml of a 25 wt. % solution of sodium methoxide in methanol to 160 ml of ethanol) was added 19.9 g (0.135 mol) of 5-(methylamino)-1,3,4-thiadiazole-2(3H)-thione and an additional 40 ml of ethanol. The mixture was warmed at approximately 30° C. for 1 hour (under a nitrogen atmosphere) followed by the addition of 25.0 g (0.132 mol) of 3-fluorobenzyl bromide and 40 ml of ethanol.

Following the initial exothermic reaction (temperature rose to approximately 40° C.), the reaction mixture was stirred under nitrogen and heated to reflux and maintained at reflux for 3 hours. Next, the volume of the mixture was reduced to approximately 90 ml by sweeping nitrogen over the heated reaction mixture (with the reflux condenser removed). The mixture was cooled to room temperature and added to 500 ml of an ice-water mixture resulting in the precipitation of a solid which was collected by vacuum filtration, washed with water and dried to yield 31.2 of crude solid product which upon recrystallization from a mixture of tetrahydrofuran and petroleum ether yielded 20.6 g of the title compound as a tan solid, m.p. 85°–87° C. The infrared and NMR spectra confirmed the structure assignment for this intermediate compound.

(B)

Preparation of
N-(5-((3-fluorophenyl)methylthio)-1,3,4-thiadiazol-2-yl)-N,N'-dimethylurea (Compound No. 1)

To a stirred solution of 19.2 g (0.075 mol) of the above intermediate dissolved in 200 ml of dry tetrahydrofuran was added 6.3 g (0.11 mol) of methyl isocyanate. The mixture was stirred at room temperature for 1.5 hours, then 2 drops of dibutyltin diacetate catalyst was added, and the mixture stirred 0.5 hours at room temperature. Next, the mixture was heated at gentle reflux for 2.5 hours after which time a vigorous exothermic reaction occurred. The reaction mixture was cooled in an ice bath. Addition of petroleum ether resulted in precipitation of a solid product which was collected by vacuum filtration, washed with petroleum ether and dried to yield 21.8 g of the title compound, m.p. 112°–116° C.

The infrared and NMR spectra confirmed the structure assignment.

EXAMPLE 2

Following essentially the procedure outlined in Example 1, the following compounds were prepared:

N-(5-((3-bromophenyl)methylthio)-1,3,4-thiadiazol-2-yl)-N,N'dimethylurea; m.p. 113°–116° C. (cpd. 2).

N,N'-dimethyl-N-(5-((3-trifluoromethylphenyl)methylthio)-1,3,4-thiadiazol-2-yl)urea; m.p. 120°–121° C. (Cpd. 3).

N-(5-((3-cyanophenyl)methylthio)-1,3,4-thiadiazol-2-yl)-N,N',dimethylurea; m.p. 110°–112° C. (cpd. 4).

N-(5-((3-chlorophenyl)methylthio)-1,3,4-thiadiazol-2-yl)-N,N'-dimethylurea; m.p. 120°–122° C. (cpd. 5).

N-(5-((4-chlorophenyl)methylthio)-1,3,4-thiadiazol-2-yl)-N,N'-dimethylurea; m.p. 140°–141° C. (cpd. 6).

N-(5-((2-fluorophenyl)methylthio)-1,3,4-thiadiazol-2-yl)-N,N'-dimethylurea; m.p. 166°–167° C. (Cpd. 7).

Other compounds within the scope of this invention may be summarized as follows:

| Cpd. | R | $R^1$ | $R^2$ |
|---|---|---|---|
| 8. | 2-CN | n-$C_4H_9$ | $CH_3$ |
| 9. | 2-$CF_3$ | i-$C_3H_7$ | i-$C_3H_7$ |
| 10. | 2-Cl | $C_2H_5$ | sec-$C_4H_9$ |
| 11. | 2-I | H | $CH_3$ |

Compounds 7 to 11 are new.

EXAMPLE 3

Cotton Defoliation

Suspensions of several compounds synthesized in Examples 1 and 2 were prepared wherein said compounds were present at a 6000 parts per million concentration by dissolving 0.3 g of each compound in 10 ml acetone and then adding distilled water containing 2000 ppm surfactant (ethoxylated sorbitan monolaurate) to a total volume of 50 ml. By further dilution with appropriate amounts of the water-surfactant mixture, suspensions having compound concentrations of 100 and 25 ppm, respectively, were prepared.

Four cotton plants (Gossypium hirsutum L. "Stoneville 213") having leaves at three to four nodes were treated with the above indicated suspensions by immersing the lower leaves in such suspensions. The plants were then removed from the suspensions and placed in a greenhouse, and after two weeks the treated plants were inspected with the results indicated in Table I.

TABLE I

| Cpd. No. | Defoliation, % (at concentration) | |
|---|---|---|
| | 100 ppm | 25 ppm |
| 1 | 100 | 100 |
| 2 | 100 | 100 |
| 3 | 100 | 75 |
| 4 | 100 | 100 |
| 5 | 100 | 100 |
| 6 | 100 | 100 |
| 7 | 37 | NT |

NT = Not Tested
Remarks: Non-treated cotton plant used as control did not defoliate over the same period of time; also, non-immersed leaves on the treated cotton plants indicated essentially no defoliating effects.

The above embodiments and examples are given to illustrate the scope and spirit of the instant invention. These embodiments and examples will make apparent, to those skilled in the art, other embodiments and examples within the scope of this invention. Therefore, the instant invention should be limited only by the appended claims.

What is claimed is:

1. A defoliating composition comprising a compound having the structural formula wherein R is F, Cl, 3-Br, 4-Br, I, CN or $CX_3$, where X is F, Cl or Br; $R^1$ is hydrogen or $C_1$–$C_4$ alkyl, and $R^2$ is $C_1$–$C_4$ alkyl; and a carrier for said compound.

2. The composition of claim 1 wherein R is F, Cl, 3-Br or 4-Br; $R^1$ is hydrogen or methyl and $R^2$ is methyl.

3. The composition of claim 2 wherein R is 3-F, 3-Cl, 3-Br or 3-$CF_3$; and $R^1$ is hydrogen.

4. A method for defoliating a plant comprising applying a defoliating amount of a compound having the structural formula wherein R is F, Cl, 3-Br, 4-Br, I, CN or $CX_3$ where X is F, Cl or Br; $R^1$ is hydrogen or $C_1$–$C_4$ alkyl; and $R^2$ is $C_1$–$C_4$ alkyl to a plant.

5. A method in accordance with claim 4 wherein said plant defoliated is cotton.

6. A method in accordance with claim 5 wherein R is F, Cl, 3-Br or 4-BR; $R^1$ is hydrogen; and $R^2$ is methyl.

* * * * *